United States Patent [19]
Bode et al.

[11] 4,107,018
[45] Aug. 15, 1978

[54] SOLID ELECTROLYTE GAS SENSOR HAVING A PROTECTIVE BONDING LAYER

[75] Inventors: James Daniel Bode, Royal Oak; Seong Kwan Rhee, Livonia, both of Mich.

[73] Assignee: Bendix Autolite Corporation, Fostoria, Ohio

[21] Appl. No.: 829,709

[22] Filed: Sep. 1, 1977

[51] Int. Cl.² ............................................. G01N 27/46
[52] U.S. Cl. .......................... 204/195 S; 204/192 SP; 427/123; 427/124; 427/125; 427/126; 427/419 A
[58] Field of Search ............. 204/195 S, 1 S, 192 SP; 60/276; 123/119 E; 324/29; 427/123, 124, 125, 126, 419 A; 29/592

[56] References Cited

U.S. PATENT DOCUMENTS

| 3,503,809 | 3/1970 | Spacil | 204/195 S X |
| 3,645,875 | 2/1972 | Record et al. | 204/195 S |
| 3,989,614 | 11/1976 | Tien | 204/195 S |
| 3,998,375 | 12/1976 | Rudd | 204/195 S X |
| 4,021,326 | 5/1977 | Pollner et al. | 204/195 S |

FOREIGN PATENT DOCUMENTS 1,545,356 9/1968 France ........................ 427/123

Primary Examiner—G. L. Kaplan
Attorney, Agent, or Firm—William G. Kratz; Raymond J. Eifler

[57] ABSTRACT

A solid electrolyte sensor for sensing oxygen in exhaust gases having a solid electrolyte body of a thimble-like design with an inner conductor thereon and a nonreactive but compatible bonding layer of magnesium or calcium oxide over the outer surface of the electrolyte body and a conductive catalyst layer superimposed on the bonding layer.

10 Claims, 2 Drawing Figures

4,107,018

SOLID ELECTROLYTE GAS SENSOR HAVING A PROTECTIVE BONDING LAYER

BACKGROUND OF THE INVENTION

Oxygen gas sensors are usable in automobile exhaust systems to monitor the oxygen content and thus the efficiency of the engine operation. A type of sensor is one, in the form of a thimble, made from a solid electrolyte which may be formed of zirconium dioxide which has conductive layers, such as a layer of platinum, on the inner surface and the outer surface. While the conductive layer on the inner surface is normally subjected to atmospheric conditions and relatively stable, the conductive layer on the outer surface is subject to the degradative effects of the high temperature flow of the exhaust gas which can lead to gradual loss of the conductive layer and decrease in the performance of the sensor. Loss of the conductive layer, such as platinum, is a particularly severe problem in automotive exhaust measurements where the large temperature and gas composition fluctuations speed the degradation. It has been proposed to place a porous protective coating over the conductive layer in order to protect that layer, such as an oxide film of magnesium-aluminum spinel, but such measures, while retarding loss of the platinum, still do not extend the life of the sensor sufficiently. Formation of a porous protective layer over the conductive layer is described in U.S. Pat. Nos. 3,645,875 and 3,978,006. Such an overlain protective layer, however, does not eliminate one of the primary reasons for platinum loss, the reaction of platinum and the solid oxide electrolyte. Under chemically reducing conditions, for example, which are found in automobile exhausts, the platinum and zirconium dioxide, when used as the electrolyte, react to form intermetallic platinum-zirconium compounds at their interface. Under subsequent oxidizing conditions, found in the same exhaust system, these compounds can revert to platinum and zirconium dioxide with a rupturing of the bonds that initially held the platinum onto the zirconium dioxide.

Automobile exhaust gases are known to vary from chemically reducing to oxidizing conditions during engine operation depending upon the driving conditions. Under accelerating conditions, relatively large amounts of unburnt hydrocarbons, carbon monoxide and hydrogen are present in the exhaust and even elemental carbon may deposit on or near the sensor. All of these components are chemically reducing and can lead to the intermetallic formation between platinum and zirconium dioxide (or other oxide electrolytes).

The problem of loss of the conductive layer, such as platinum, on a solid electrolyte is discussed in U.S. Pat. No. 3,989,614 which teaches use of a porous electronic conductor over the outer surface of a solid electrolyte tube, where the electronic conductor is a transition metal oxide. The porous coating is of an electronic conductor impervious to oxygen ions and hydrogen molecules. This porous coating is applied to the surface of the solid electrolyte in such a manner that voids are present in the coating, with solid electrolyte being exposed which is then directly contacted with the platinum catalyst that is subsequently placed over the sensor. There are thus areas on the surface of the electrolyte which are coated by the transition metal oxide and the catalyst, areas which are coated by the transition metal oxide only, and other areas which are covered by the platinum catalyst only, as clearly shown in the drawing of that patent. While this system employs a coating of transition metal oxide over the solid electrolyte and a catalyst layer therefor, as described, there are specific areas of direct contact of platinum catalyst and solid electrolyte at which intermetallic platinum-electrolyte compound formation and subsequent degradation could occur.

An object of the present invention is to provide an improved solid electrolyte sensor where reaction between the solid electrolyte and the catalyst layer is prevented by the use of a porous, nonreactive but compatible protective bonding layer between those components.

The introduction of a protective bonding layer will also improve the catalytic nature of the platinum electrode. Oxygen gas sensors in automobile exhausts ordinarily are designed to measure the net, equilibrium amount of oxygen in the hot gas. Thus, the outer surface of the sensor must be catalytic to complete all possible combustion reactions in the gas to be measured. The outer platinum electrode commonly acts as a catalyst as well as an electrical conductor. The catalytic efficiency of the platinum electrode will greatly depend upon its surface area. While such electrodes are initially applied in a manner that will give it the greatest surface area possible on the limited area of the sensor element, with continued used at high temperatures, the platinum slowly agglomerates so as to reduce the exposed surface area thereof. This is a further form of degradation of the sensor. With the use of the porous, nonreactive but compatible protective bonding layer of the present invention, the surface area of the platinum electrode is greatly increased and the efficiency of its catalytic activity prolonged.

With the use of the protective bonding layer interposed between the solid electrolyte and the platinum catalyst, the availability of embedding particles of platinum in the surface of the protective bonding layer further improves adherence of the platinum electrode to the sensor.

SUMMARY OF THE INVENTION

The present invention provides an improved element for sensing oxygen, and a method of its formation, with an electrolyte sensor element s comprised of a solid electrolyte body 1 for transferring oxygen atoms, the inner surface of the body 1 having conductive means 3 thereon such as a conductive platinum film characterized in that a nonreactive but compatible bonding layer 5 of magnesium oxide or calcium oxide is provided on the outer surface of the electrolyte body 1 and a conductive catalyst layer 7, such as a platinum catalyst, is superimposed over the bonding layer 5.

DETAILED DESCRIPTION

The oxygen sensor of the present invention provides for better adherence and protection of the outer conductive catalyst from contact with the solid electrolyte under changing conditions of operation.

Figure 1:
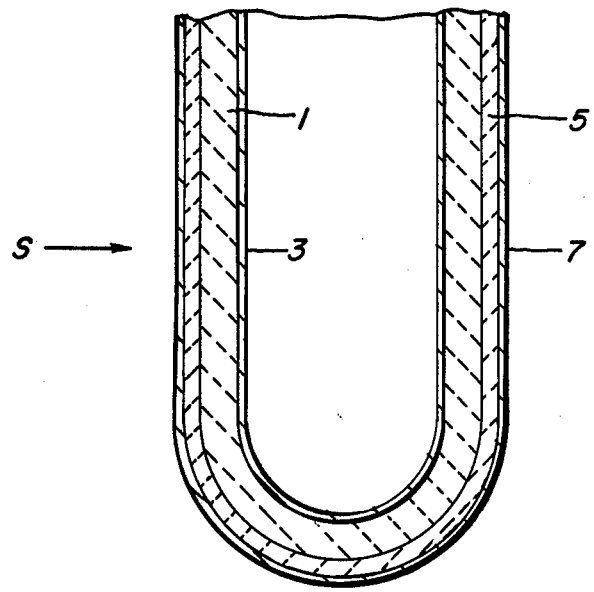
FIG. 1 is a schematic, cross-sectional view of a sensor electrode element constructed in accordance with the present invention.
Figure 2:
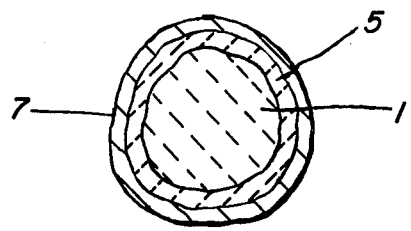
FIG. 2 is an enlarged plan view of a cut-away portion of the outer surface of the element of FIG. 1 exposing the various layers thereon.

Referring to FIG. 1, there is illustrated an oxygen sensor element s prepared in accordance with the present invention, where a generally hollow tube or thimble-like solid electolyte body 1 for transferring oxygen ions is provided composed of known oxygen-ion transferring material of the art. Zirconium dioxide is a preferred solid electrolyte for the body 1, while the same may incorporate various known stabilizing materials such as yttrium oxide, thorium dioxide, calcium oxide or the like, with the body, as is known, being open at one end for entrance of reference gas, such as the atmosphere, while the other end is closed and inserted into the exhaust gases to be monitored. The inner surface of the solid electrolyte body 1 has a conductive means 3 thereon which may be a strip of conductive material or a layer or film of conductive material, such as platinum, and which is applied to the inner surface of the body 1 by known methods.

A nonreactive but compatible bonding layer 5 is provided on the outer surface of the electrolyte body 1, this layer 5 providing for good adherence of the outer conductive catalyst 7 while spacing the latter from the solid electrolyte body 1. The porous, protective bonding layer 5 is preferably of magnesium oxide since this material does not react with platinum metal even under chemically reducing conditions at very high temperatures and is compatible with zirconium dioxide, often being used to stabilize zirconium dioxide ceramics. Also, magnesium oxide does not interfere with the ionic conductivity of zirconium dioxide and reportedly shows ionic conductivity itself, and can serve as a bridge between the platinum electrode and the sensor electrolyte while at the same time blocking deleterious chemical reactions between the two. Another alkaline earth metal, calcium, can also be used in its oxide form in the protective bonding layer, or mixtures of magnesium and calcium oxides used.

The alkaline earth metal oxide may be applied directly as a layer to the solid electrolyte body such as applying an aqueous slurry thereof by dipping, spraying or painting. Or, other forms of the alkaline earth metal compounds may be applied to the body which upon firing will form the oxide, for example magnesium or calcium carbonates, hydroxide, nitrate or other decomposable inorganic compounds as well as organic compounds such as magnesium or calcium acetate, propionate, oxalate, or the like. By using such decomposable compounds, the temperature or time needed to fire the layer onto the sensor element may be reduced as well as the adherence and porosity of the layer enhanced. The compounds usable would be those which will fire to form a porous, adherent layer on the solid electrolyte body, without interfering with the electrolytic action of the sensor or reacting with the platinum conductive catalyst.

An alternate means of applying the alkaline earth metal oxide is by sputtering the oxide directly onto the solid electrolyte or by reactive sputtering of the metal in an oxygen atmosphere using known techniques of sputtering. Sputter deposition of the oxide could be accomplished in the same sputtering apparatus used to subsequently apply the outer conductive catalyst layer, thus simplifying the sensor fabrication procedure and, at the same time, assuring intimate and firm bonding between the solid electrolyte body, the protective bonding layer and the outer conductive catalyst layer.

The outer conductive catalyst layer 7 is then superimposed over the protective bonding layer 5. The conductive catalyst layer 7 is platinum or a platinum family catalyst which is applied over the layer 5, after firing thereof to a temperature of about 2800°–3000° F, to provide a conductive and catalytic film. This layer 7 may be applied by known methods, such as vapor deposition, sputtering, spraying, painting or the like. In one embodiment, platinum may be applied as a paste to the protective bonding layer before the latter is fired at about 2800°–3000° F so that particles of platinum are physically adhered to the protective layer with subsequent deposition of the platinum layer on this formation to provide direct platinum to platinum bonding points for additional bonding of the conductive catalyst layer superimposed thereover.

The protective bonding layer, used in the present construction, does not interfere with the application or function of the outer electrically conductive layer or any additional protective over-layer which may be placed over the outer electrically conductive layer to further enhance the durability of the same.

The resultant sensor element comprises a solid electrolyte body with a protective bonding layer over the outer surface thereof and a conductive catalyst layer superimposed thereover. The protective bonding layer is applied as an integral part of the solid electrolyte and with the conductive catalyst layer thereon to provide improved sensor performance. The construction can prolong the active life of the sensor by preventing deleterious chemical reactions that would otherwise occur between the outer platinum electrode and the solid electrolyte, it can prolong the sensor life by providing a much greater surface area to enhance and extend the desired catalytic activity of the external electrode, the conductive catalyst layer, and, with platinum particles embedded in the surface of the protective bonding layer, the bonding layer can act as an anchor to further improve adherence of the platinum electrode to the sensor.

We claim:

1. In a solid electrolyte sensor element for sensing oxygen wherein the element comprises a solid electrolyte body for transferring oxygen ions, the body having an inner surface with conductive means thereon, the improvement comprising a nonreactive but compatible bonding layer of an oxide of an alkaline earth metal selected from the group consisting of magnesium and calcium or a mixture thereof, on the outer surface of said solid electrolyte body and a conductive catalyst layer superimposed on said bonding layer.

2. In a solid electrolyte sensor element as defined in claim 1, the improvement wherein said solid electrolyte body comprises zirconium dioxide.

3. In a solid electrolyte sensor element as defined in claim 1, the improvement wherein said oxide of an alkaline earth metal is magnesium oxide.

4. In a solid electrolyte sensor element as defined in claim 3, the improvement wherein said conductive catalyst layer comprises platinum.

5. In a method of forming a solid electrolyte sensor element for sensing oxygen having a solid electrolyte body with an inner surface having a conductive means thereon, the improvement comprising:

applying to the outer surface of said solid electrolyte body a nonreactive but compatible layer of an oxide of an alkaline earth metal selected from the group consisting of magnesium and calcium oxide or a mixture thereof; and applying a conductive catalyst layer over said layer of oxide.

6. In the method of forming a solid electrolyte sensor element as defined in claim 5, the improvement wherein said alkaline earth metal oxide is applied to said electrolyte body as a decomposable alkaline earth metal compound and heating said alkaline earth metal compound to decompose the same and form said oxide.

7. In the method of forming a solid electrolyte sensor element as defined in claim 5, the improvement wherein said conductive catalyst layer comprises platinum.

8. In the method of forming a solid electrolyte sensor element as defined in claim 7, the improvement comprising applying platinum particles to said alkaline earth metal oxide layer and heating the same to firing temperature and applying a subsequent layer of platinum thereover.

9. In the method of forming a solid electrolyte sensor element as defined in claim 5, the improvement comprising applying said alkaline earth metal oxide to said electrolyte body by direct sputtering.

10. In the method of forming a solid electrolyte sensor element as defined in claim 5, the improvement comprising applying said alkaline earth metal oxide to said electrolyte body by reactive sputtering.

* * * * *